United States Patent [19]

Marks

[11] Patent Number: 5,108,420
[45] Date of Patent: Apr. 28, 1992

[54] APERTURE OCCLUSION DEVICE
[75] Inventor: Lloyd A. Marks, Bryn Mawr, Pa.
[73] Assignee: Temple University, Philadelphia, Pa.
[21] Appl. No.: 649,593
[22] Filed: Feb. 1, 1991
[51] Int. Cl.[5] ............................................. A61B 17/00
[52] U.S. Cl. .................................... 606/213; 606/78; 606/151; 606/157
[58] Field of Search ................. 606/78, 151, 157, 158, 606/215, 108, 213; 128/898, 628, 686, 843, 831

[56] References Cited

U.S. PATENT DOCUMENTS

| | | |
|---|---|---|
| 3,868,956 | 3/1975 | Alfidi et al. |
| 3,874,388 | 4/1975 | King et al. |
| 4,007,743 | 2/1977 | Blake |
| 4,170,990 | 10/1979 | Baumgart et al. |
| 4,425,908 | 1/1984 | Simon |
| 4,503,569 | 3/1985 | Dotter |
| 4,512,338 | 4/1985 | Balko et al. |
| 4,707,196 | 11/1987 | Honma et al. |
| 4,710,192 | 12/1987 | Liotta et al. |
| 4,744,364 | 5/1988 | Kensey |
| 4,758,222 | 7/1988 | McCoy |
| 4,805,618 | 2/1989 | Ueda et al. ............... 128/831 |
| 5,037,427 | 6/1991 | Harada et al. ............ 608/108 |

OTHER PUBLICATIONS

"Nonsurgical Placement of Arterial Endoprotehses: A New Technique Using Nitinol Wire", Cragg et al., Radiology, 147, 261-263, 1983.
"Metals That Remember", Steven Ashley, Popular Science, Jan. 1988.
"The Biocompatibility of Nitinol", L. S. Castleman et al., Biocompatibility of Clinical Implant Materials, chap. 5, pp. 129-154.
"Nonsurgical Implantation of a Vascular Ring Prosthesis Using Thermal Shape Memory Ti/Ni Alloy (Nitinol Wire)", Yoichi Sugita et al., vol. XXXII, Trans Am Soc Artif Intern Organs, 1986.
"Transluminal Expandable Nitinol Coil Stent Grafting: Preliminary Report"; Charles T. Dotter, M.D. et al., Radiology 147: 259-260, Apr. 1983.
"A New Percutaneous Vena Cava Filter", Andrew Cragg et al., AJR 141, 601-604, Sep. 1983.
"Transvenous Atrial Septal Defect ...", Sideris et al., Abstract from the American Heart Assoc. Mtg., Nov. 1988.
"A Trial Septal Defects: Anatomic Study ...", Rome et al., Abstract from the American Heart Assoc. Mtg., Nov. 1988.
"Nonsurgical Closure of PDA: Clinical Application of the Rashkind PDA Occluder System", Rashkind et al., Circulation, vol. 75, No. 3, Mar. 1987.
"Percutaneous Catheter Closure of the Ductus Arteriosus in Children and Young Adults", A.J.C. 64, Jul. 1989.
"Outpatient Closure of the Patent Ductus Arteriosus", Wessel et al., Circulation, No. 5, May 1988.
"Transcatheter Umbrella Closure of Congenital Heart Defect", Lock et al., Circulation, 75, No. 3, Mar. 1987.
"Transcatheter Closure of Atrial Septal Defects", Lock et al., Circulation, 79, No. 5, May 1989.
"Nonsurgical Therapy of Cardiac Disorder", Ruttenberg, Pediatric Consult, 5, No. 2, 1986.

Primary Examiner—Stephen C. Pellegrino
Assistant Examiner—Gary Jackson
Attorney, Agent, or Firm—Ratner & Prestia

[57] ABSTRACT

A device consisting of a wire for occluding an aperture within a body surface, such as atrial and ventricular septal defects (and the method of using such a device). The wire comprises two configurations, an elongated configuration for passage into said body through a catheter and through the aperture, and a preprogrammed configuration including occlusion-forming wire segments, one on each side of said aperture. The wire also includes means (preferably a temperature-induced shape change) for changing the wire from the elongated configuration to the preprogrammed configuration in the body.

14 Claims, 3 Drawing Sheets

APERTURE OCCLUSION DEVICE

FIELD OF THE INVENTION

The invention relates to devices and methods used to occlude (i.e. block blood flow through) an aperture within a body surface; specifically, it relates to devices and methods to occlude cardiovascular septal defects.

BACKGROUND OF THE INVENTION

It is often necessary to occlude a defect or an aperture within a body surface, such as a wall or membrane separating cavities within the body. A typical example is a congenital heart lesion called an atrial septal defect. This is a hole, between the two upper chambers of the heart, which must be closed.

King et al., U.S. Pat. No. 3,874,388, and Blake, U.S. Pat. No. 4,007,743 disclose a stainless steel apparatus for closing a shunt in the vascular system. The dual umbrella apparatus has six ribs which retain the umbrella in an open position. The King et al. apparatus has "barbs" at the ends of the ribs which anchor onto the tissue surrounding the shunt. Alternatively, the barbs on the ribs of one umbrella may insert into holes on the ribs of the second umbrella, see FIG. 15A. The Blake apparatus has pivotally mounted struts which provide a flat surface to which a disk may be secured.

In "A New Percutaneous Vena Cava Filter", Cragg et al. disclose a filter composed of nitinol which when inserted into the inferior vena cava, traps emboli and clots. In the process of placing the filter, there is the threat of dislodging thrombi when the catheter or guide wire is advanced too far.

Lock et al., in *Circulation*, disclose a spring-loaded clamshell occluder of several sizes. The tension in the arms is manually controlled during delivery such that the arms of the distal umbrella, the one inserted first, are everted during placement, creating a cone.

The Rashkind occluder has two polyurethane foam disks mounted on surgical steel wire assemblies. The occluder is used to seal off the ductus arteriosus and is disclosed in *Circulation*. Vol. 75., page 583, *American Journal of Cardiology*, Vol. 64, page 218, and *Circulation*, Vol. 77, page 1068.

Devices currently used to occlude septal defects, including those indicated above, have been known to dislodge and embolize.

BRIEF DESCRIPTION OF THE INVENTION

The present invention comprises an aperture occlusion device which includes a wire having two configurations, an elongated configuration for passage through a catheter and through the aperture, and a second, preprogrammed, configuration. In the second configuration, two occlusion-forming wire segments oppose one another. These are adapted to be deployed on each side of the aperture to be occluded. A means for changing the wire from the elongated configuration to the preprogrammed configuration inside the body is further included. Typically, this may consist of a thermally responsive wire composition, the wire being preprogrammed so that at a certain temperature (body temperature for example), the wire, which is normally straight at other temperatures assumes a different ("preprogrammed") shape or configuration. Each occlusion-forming wire segment is adapted to press toward the opposing segment, thereby closing or occluding the aperture. Apertures or openings in other walls or membranes within the body or abnormally patent blood vessels may be similarly occluded.

In one embodiment, the occlusion-forming wire segments may comprise essentially flat helices, urged toward one another. In another embodiment, the wire may further include two foldable membranes, one associated with each occlusion-forming wire segment. The membranes are folded for transport through the catheter along with the wire. Upon conversion of the wire to its preprogrammed configuration, the membranes unfold onto a frame produced by the occlusion-forming wire segments, one on each side of the aperture.

Also included in the invention is a method for occluding an aperture by positioning a catheter at the distal side of the aperture and deploying a wire therethrough in an elongated configuration, (with the aid of a means for holding the wire) to the distal side of the aperture. Upon exiting the catheter, the wire converts to a preprogrammed configuration including an occlusion-forming wire segment on the distal side of the aperture. Upon continued deployment in the elongated configuration, the wire is permitted to assume the preprogrammed configuration including an opposing occlusion-forming wire segment on the proximal side of the aperture, with the two segments pressing toward one another. The wire is then disengaged from the means for holding the wire.

DETAILED DESCRIPTION OF THE INVENTION

The invention includes devices and methods for occluding apertures in body surfaces, such as walls or membranes; the devices are adapted to be passed into the body through a catheter and through the aperture. Such apertures are openings, often congenital defects, connecting two cavities of the body. Fallopian tubes may also be occluded by using the devices and methods of the claimed invention. Cardiac septal defects are the type of apertures for which the preferred embodiments of the invention are designed. For example, the devices and methods of the present invention may be used to occlude a ventricular septal defect or an unwanted vascular communication such as a patent ductus arteriosus.

An essential part of the present invention is a wire having two configurations, an elongated configuration or folded configuration for passage into the body through a catheter and through the aperture, and a preprogrammed configuration including occlusion-forming wire segments one on each side of the aperture. This wire also includes a means for causing it to change from the elongated configuration to the preprogrammed configuration inside the body. The device may also be combined with a catheter means for introducing the wire into the body. The catheter includes means for holding the wire, such as a release wire, while it is in the catheter and before it has been stimulated to convert to the preprogrammed configuration.

Preferably the wire is composed of a shape memory retentive material, such as nitinol, which causes the wire to change configurations, in response to a temperature change and which enables the wire to be activated at body temperature (having previously been at a different temperature) to assume a preprogrammed configuration. Spring steel may also serve this purpose. Furthermore, the wire must be biocompatible, and may be coated with Teflon, fibrin or endothelial cells, for example.

The occlusion forming wires may be associated with a foldable membrane, either by being embedded in the membrane or secured (by glue, stitches, staples or the like) to the surface thereof. In this embodiment, the membrane is transportable through a catheter in a folded configuration along with the wire. The occlusion-forming wires are adapted, upon converting to preprogrammed configuration, to unfold the membranes and to form a frame to support the membranes as domed or umbrella-shaped members on each side of the aperture. In another embodiment, the occlusion-forming wire is not attached to a membrane, and forms coiled helices, one on either side of the defect and urged toward each other.

Figure 1:
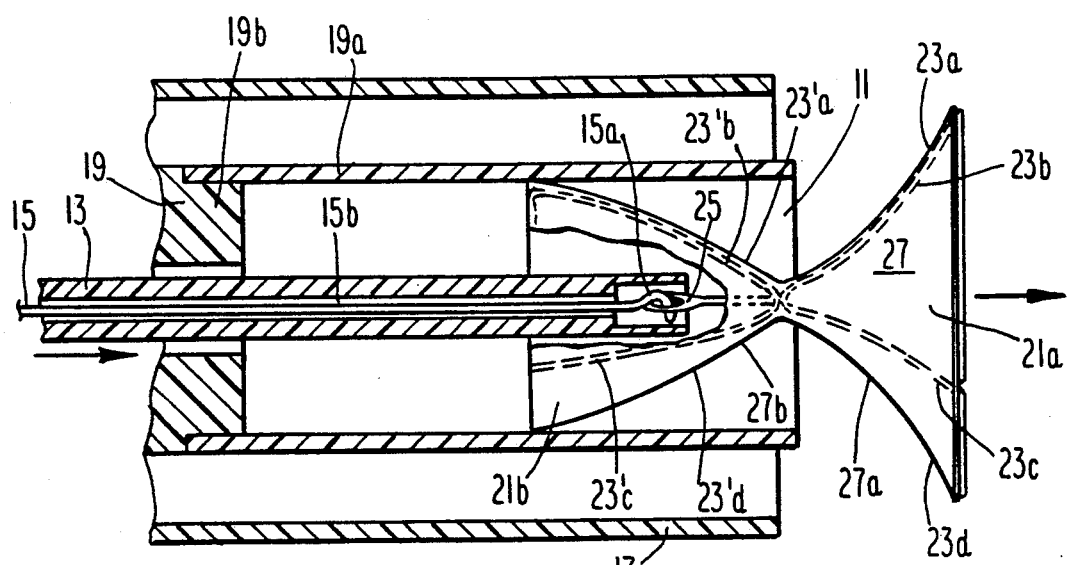
FIG. 1 is a schematic cross-sectional view, during deployment, of one embodiment of the aperture occlusion device of the claimed invention.

Referring to FIG. 1, there is shown a partially deployed stage of one aperture occlusion device. As would be used for the occlusion of a septal defect, sheath 17 (a large catheter), after entering the body in a conventional manner, such as through a femoral vein, enters the heart via the inferior vena cava and is positioned on the distal side of an atrial septal defect in the body of the left atrium.

Release wire 15, including shaft 15b and knuckle 15a, device engaging catheter 13 and aperture occlusion device 27, all disposed within deployment catheter 19, are prepared as a unit prior to deployment through sheath 17 and introduced into the body either along with or later through sheath 17.

Aperture occlusion device 27 is composed of two biocompatible membranes 21a and 21b, each comprised of a thin polyurethane membrane film, for example. Preprogrammed shape memory retentive, wire ribs 23 and 23' are secured (and may be threaded, sewn or sandwiched) to each biocompatible membrane 21a and 21b. Eye 25, attached to wire ribs 23 and 23', extends from the center of aperture occlusion device 27 and engages knuckle 15a of release wire 15. One half of aperture occlusion device 27b is seen in the folded state; upon release from deployment catheter 19 and contact with body temperature, the membrane expands between the ribs, as shown by device half 27a with associated ribs 23. In FIG. 1, four wire ribs, 23a-d and 23'a-d, on each half of device 27, unfold, i.e. are converted from their elongated configuration to a second preprogrammed configuration, such as by a thermally stimulated shape change to a preprogrammed configuration, which urges the wire ribs outwardly, to expand and release. For this purpose, ribs 23a-d and 23'a-d are composed of a thermally responsive shape, shape memory retentive material, such as nitinol.

For transport to the site of deployment, the unit including release wire 15, device engaging catheter 13 and aperture occlusion device 27 are channeled into pod 11 of deployment catheter 19. Deployment catheter 19 includes an inner plastic portion 19b integrally connected to outer metal portion 19a. Release wire 15, device engaging catheter 13 and aperture occlusion device 27 are retained together and folded in deployment catheter 19. In practice, device 27 may be deployed without the use of deployment catheter 19, so long as sheath 17 is in a cold environment thus prohibiting device 27 from forming the preprogrammed shape.

In use, the assembly including release wire 15, device engaging catheter 13, aperture occlusion device 27 and deployment catheter 19 are passed through sheath 17 until the distal half of device 27 is disposed on the distal side of the septal defect (i.e. "aperture") to be occluded. Device engaging catheter 13, release wire 15, and aperture occlusion device 27 are maintained in place on the distal side of the defect while sheath 17 is retracted back through the defect to the proximal side thereof. Device engaging catheter 13 and release wire 15 are advanced freeing 27a to expand to preprogrammed shape. This enables a thermally stimulated shape change to the preprogrammed deployed configuration of ribs 23a-d. One-half of aperture occlusion device, 27a, is thus deployed on the distal side of the septal defect.

Coincident with the pull-back movement of deployment catheter 19 either in the preceding step or in the following step, sheath 17 is also retracted away from the aperture to be occluded.

Aperture occlusion device 27 is then pulled taut against the defect such that four wire ribs 23a-d expand and contact the heart tissue around the defect. Optionally, sheath 17 is then pulled back further away from the proximal side of the defect (if that had not been done earlier), and deployment catheter 19 is retracted leaving device engaging catheter 13, release wire 15, and aperture occlusion device 27 in place and thus exposing aperture occlusion device half 27b on the proximal side of the defect, at which point the second half 27b of device 27 is deployed.

Once aperture occlusion device 27 is fully deployed, as seen in FIGS. 2-5, knuckle 15a is disengaged from eye 25 of aperture occlusion device 27, by retracting catheter 13 slightly from eye 25. The assembly including deployment catheter 19, device engaging catheter 13 and release wire 15 are then retracted from sheath 17. Finally, sheath 17 is also retracted from the body.

Figure 2:
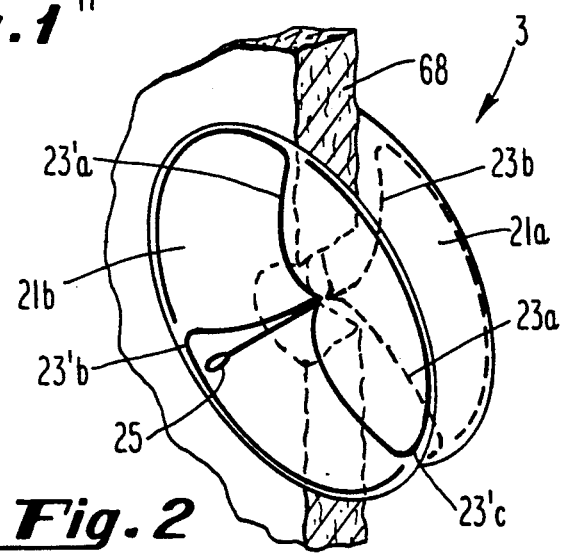
FIG. 2 is a perspective view of another aperture occlusion device of the present invention in a fully deployed configuration.

FIG. 2 depicts a perspective view of an aperture occlusion device, with 3 ribs, like that seen in FIG. 1, but fully deployed to occlude a defect or aperture 68 in wall 68a. Membranes 21a and 21b are supported by wire ribs 23a-c and 23'a-c respectively, which urge the membranes toward each other and connect the membranes with eye 25.

Figure 3:
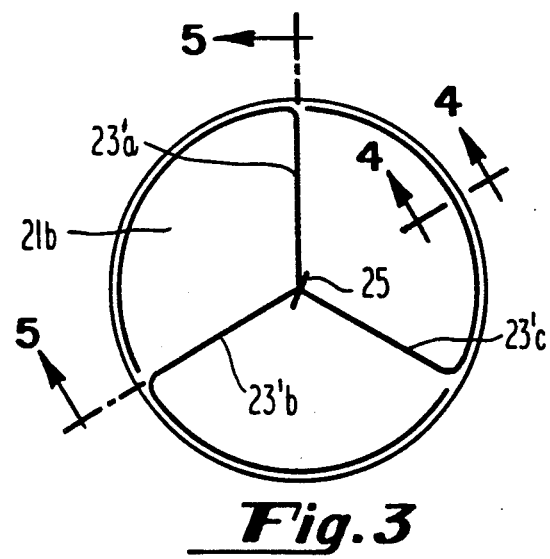
FIG. 3 is planar view of the device shown in FIG. 2.

As seen in FIG. 3, membrane 21a is attached to three wire ribs 23a, b and c extending circumferentially then curving and radially extending to the center of membrane 21a. Ribs 23a-c attach at the center of membrane 21a and connect the pair to each other and to eye 25 which attaches to a release wire, not shown. Ribs 23a–c, upon thermal triggering of the memory retentive properties of the rib material (preferably nitinol), support and maintain the shape of membrane 21a. Membrane 21b is similarly retained by ribs 23'a–c.

Figure 4:
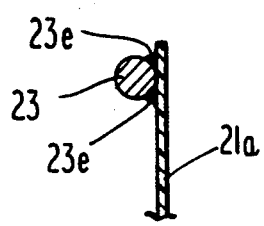
FIG. 4 is an enlarged cross-sectional view, in the plane 4—4 of FIG. 3.

FIG. 4 is a cross-section through plane 4—4 of FIG. 3. As depicted therein, membrane 21a is secured to rib 23a by glue 23e. Stitches, staples or the like may also be used to affix membrane 21a to rib 23a. Other configurations of ribs 23a, b, c may also be used.

Figure 5:
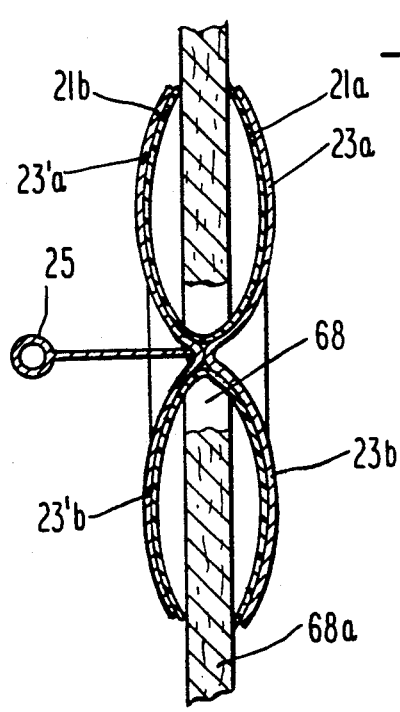
FIG. 5 is a cross-sectional view, in plane 5—5, of the fully deployed aperture occlusion device shown in FIG. 3.

FIG. 5 illustrates a cross-section along plane 5—5 of the aperture occlusion device of FIG. 3. Membranes 21a and 21b occlude aperture 68 in wall 68a, and are supported by wire ribs, 23a, b and 23'a, b, which urge the membranes toward each other and connect the membranes with eye 25.

Figure 6:
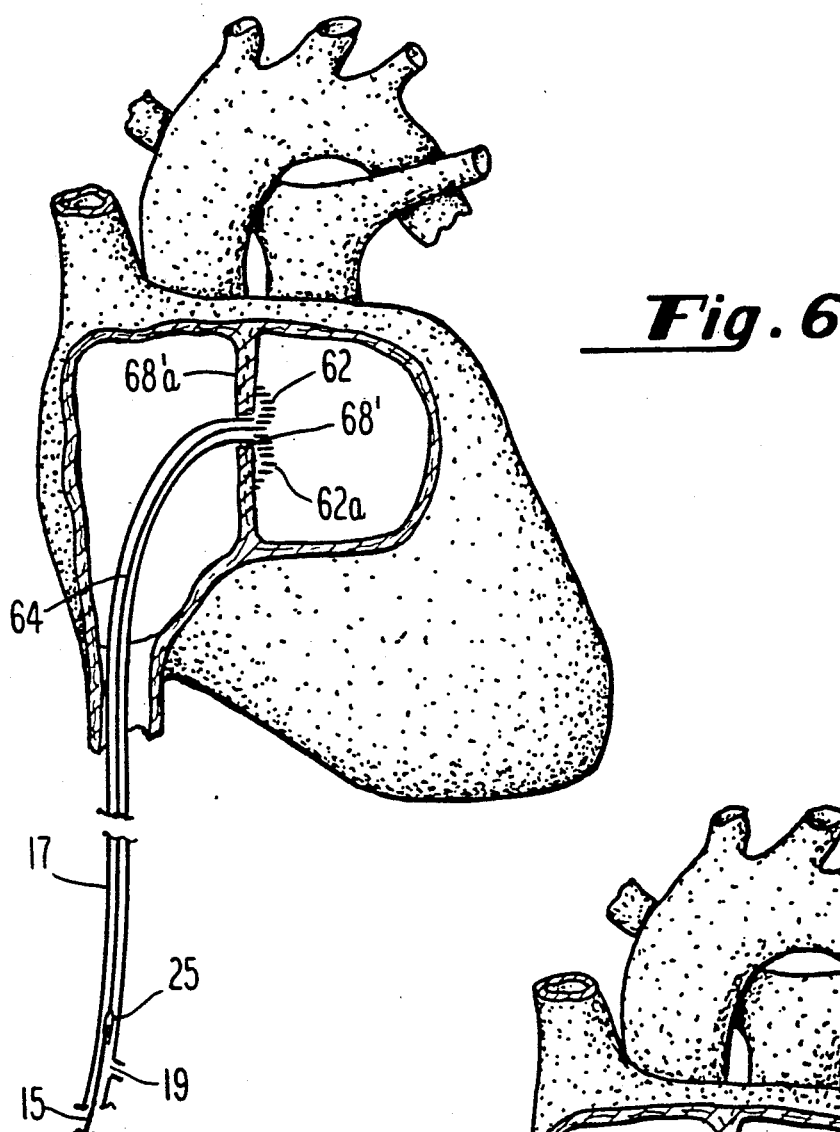
FIG. 6 is a perspective view of a heart, partially in cross-section, schematically showing an atrial septal defect and an occlusion device of the present invention partially deployed.

FIG. 6 depicts septal defect 68' with a double helix occlusion device 62 partially deployed. Device 62 is introduced as a straight wire 64 through the assembly including, device engaging catheter 13 (like that shown in FIG. 1, but not shown in FIG. 6 due to limited space available), release wire 15 and sheath 17. Sheath 17 is diametrically larger than device engaging catheter 13 to allow passage of device engaging catheter 13 therethrough. As with the assembly shown in and described with respect to FIG. 1, the assembly of release wire 15, device engaging catheter 13, wire 64 and sheath 17 are introduced through a large vein to and through the defect to be occluded. Sheath 17 optionally may be stopped short of defect 68' and may be withdrawn with device engaging catheter 13, as described, or independently of catheter 13.

Helix 62a is formed on the distal side of defect 68', preferably by the coiling of wire 64, nitinol for example, in response to a temperature change, upon body temperature contact or by retraction of spring steel into its "relaxed" (preprogrammed) configuration. A plurality of coils of progressively smaller diameter are formed, finally contacting the periphery of atrial wall 68a' surrounding defect 68' on the distal side thereof; each such coil of wire 64 contacts the previously formed coil above and below defect 68', such that helix 62a is deployed from the outside in, (relative to defect 68), until helix 62a is formed (as seen in FIG. 6).

Figure 9:
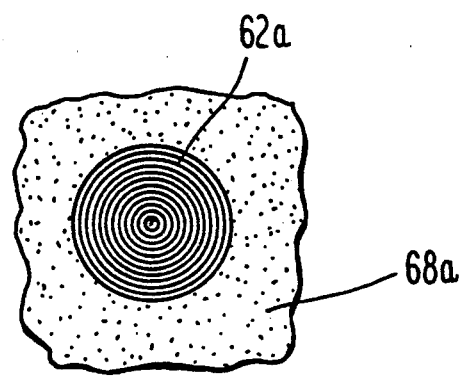
FIG. 9 is a planar view of the aperture occlusion device of FIG. 8.

The aperture occlusion device of FIG. 6 after deployment into the left atrium is seen in FIG. 9. The concentric circles are the result of the coiling of wire 64 (in this case from a very small starting circumference out) and also contacting the previously formed coil above and below defect 68', this time on the proximal side thereof.

Figure 7:
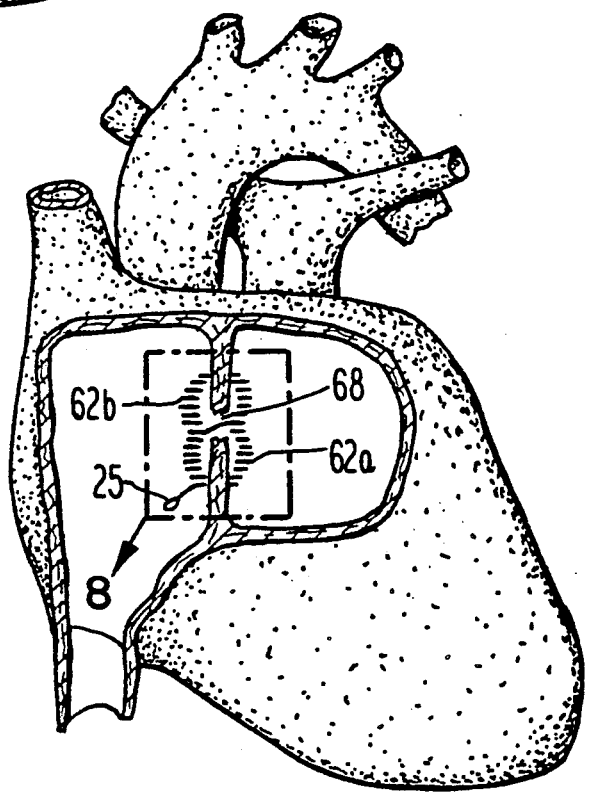
FIG. 7 is similar to FIG. 6, with the occlusion device fully deployed.
Figure 8:
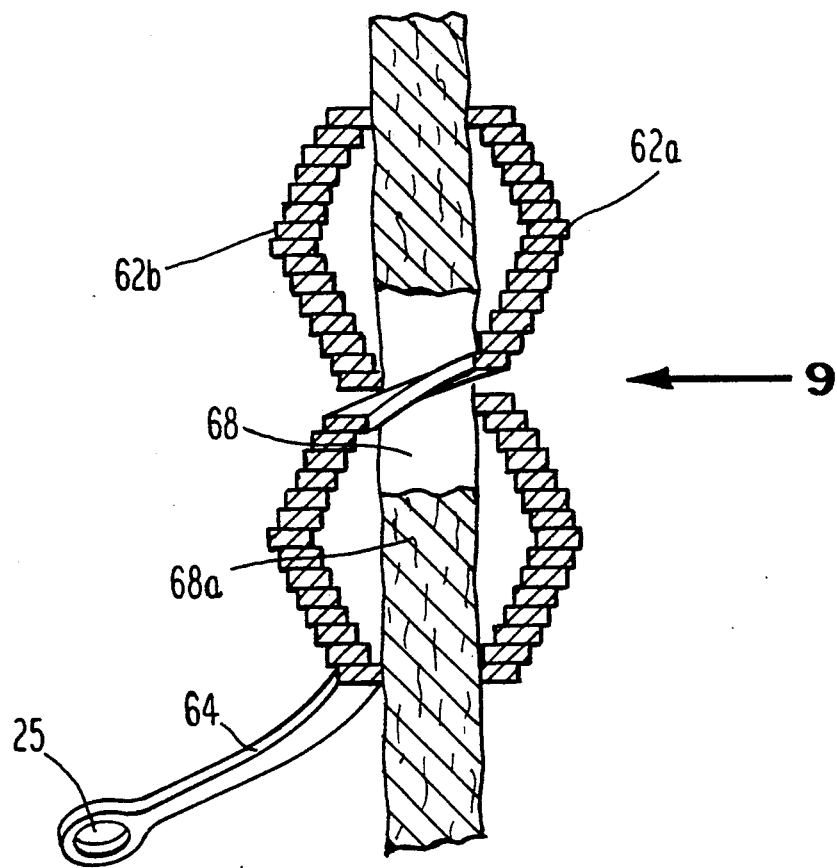
FIG. 8 is an enlarged cross-sectional view of the deployed aperture occlusion device shown in FIG. 7.

After deploying helix 62a on the distal side of defect 68, sheath 17, device engaging catheter 13, release wire 15, and wire 64 are withdrawn equally and together to bring helix 62a into firm contact with the septal surface. As tension is maintained on wire 64 via release wire 15, sheath 17 is withdrawn over wire 64 and release wire 15, thereby exposing a length of wire 64 on the proximal side of the defect. Tension on wire 64 is then slowly reduced by advancing release wire 15 and sheath 17 equally and together. Wire 64 begins coiling at or near septal surface below defect 68. By progressively reducing tension on wire 64 (by repetitively withdrawing sheath 17 over release wire 15 and advancing sheath 17 and release wire 15 equally and together), successive coils are formed, each moving outward beyond the previously formed coil. Thus, helix 62b is formed from the inside out, until helix 62b is fully deployed as seen in FIGS. 7 and 8. Eye 25 is then disengaged from the release wire 15 (not shown), and the remaining apparatus is removed from the body as described with respect to FIG. 1.

In those embodiments dependent upon a thermally responsive change (such as with nitinol) as the means for effecting device deployment, it is desirable prior to deployment to continuously infuse a biocompatible fluid (such as normal saline) which is substantially below body temperature (for example at room temperature) through side port 19 of sheath 17 to maintain a thermal environment within sheath 17, that is below the transition temperature of the thermally responsive wire 64. This assures that wire 64 will not assume its programmed shape until it exits sheath 17.

Furthermore, the programmed deployed configuration of the double helix coil (in the embodiment of FIGS. 6–9) may preferably include shaping to urge the outermost coils of helices 62a and 62b inward toward the septal surface (and one another) to provide an increased frictional force between the helices and their respective septal surfaces.

By way of general description of the method of this invention, the device of the present invention may be used in a method of occluding an aperture within a body surface. A catheter, which can accommodate a wire in an elongated or folded configuration (optionally with an associated membrane), is introduced through a body member such as a femoral vein, deployed, for example, into the heart through the inferior vena cava and manipulated into position on the distal side of the aperture where the wire assumes its preprogrammed configuration including an occlusion-forming wire segment urged toward the aperture on the distal side of the septal defect. Withdrawing the catheter partially over the wire allows a substantial length of the wire to be exposed on the near side of the defect. Upon further deployment, the wire assumes a preprogrammed configuration including an occlusion-forming wire segment urged toward the aperture on the proximal side of the aperture. The wire is then disengaged from the means for holding it.

The device and method of this invention are believed to be particularly well adapted to occlude both atrial and ventricular septal defects, as well as other cardiovascular openings, such as a patent ductus arteriosus. The device (modified for tubal rather than aperture occlusion) is also well suited for use in occluding fallopian tubes.

In the embodiments disclosed, the finished structure comprises two connected occlusion-forming wire segments, disposed on opposite sides of an aperture, each formed of a wire resulting in helices, or domed members (with membranes attached to a wire frame), urged toward one another.

While this invention has been disclosed with reference to specific embodiments, it is apparent that other embodiments and equivalent variations of this invention may be devised by those skilled in the art without departing from the true spirit and scope of this invention. The appended claims are intended to be construed to include all such embodiments and equivalent variations.

What is claimed is:

1. A device adapted to occlude an aperture within a body surface, and adapted to be passed into said body, through a catheter and through said aperture, said device comprising a wire having two configurations, an elongated configuration for passage through said catheter and through said aperture, and a preprogrammed configuration which includes occlusion-forming wire segments one on each side of said aperture urged toward one another and means for causing said wire to change from said elongated configuration to said preprogrammed configuration inside said body, said means being a temperature responsive material of construction of said wire, by which said wire is activated at body temperature, to assume said preprogrammed configuration.

2. A device of claim 1 wherein said wire is combined with a catheter means for introducing said wire into said body, said catheter means also includes means for holding said wire, while it is in said catheter, at a temperature at which said wire does not tend to assume said preprogrammed configuration.

3. A device of claim 1 wherein said occlusion-forming segments each comprise helical coils urged toward one another.

4. A device of claim 1 wherein said wire further includes two foldable membranes, one associated with said first occlusion-forming wire segment and the other associated with said second occlusion-forming wire segment, said membranes in folded configuration being transportable through a catheter along with said wire, said wire adapted upon converting from said elongated configuration to said preprogrammed configuration to unfold said membranes and to form a frame supporting said membranes as essentially planar members, one disposed on each side of said aperture, and urged toward one another, wherein said means for causing a change in configuration is a thermally responsive material of construction.

5. A device according to claim 4 wherein said wire is secured to said membranes of said occlusion-forming wire segments.

6. A device according to claim 1, wherein said wire consists of nitinol.

7. A device according to claim 1, wherein said wire is biocompatible.

8. A device according to claim 1, wherein said wire is coated to enhance biocompatibility.

9. A device adapted to occlude an aperture within a body surface, and adapted to be passed into said body, through a catheter and through said aperture, said device comprising a wire having two configurations, an elongated configuration for passage through said catheter and through said aperture, and a preprogrammed configuration which includes occlusion-forming wire segments one on each side of said aperture, and means for causing said wire to change from said elongated configuration to said preprogrammed configuration inside said body, wherein said occlusion forming segments each comprise helical coils urged toward one another.

10. A device according to claim 9, wherein said wire consists of spring steel.

11. A method for occluding an aperture within a body surface by positioning the end of a catheter at the distal side of the aperture, deploying a wire of temperature responsive material of construction in an elongated configuration through said catheter to the distal side of said aperture with the aid of a means for holding said wire, permitting the wire exposed thereby to assume a preprogrammed configuration, including an occlusion-forming wire segment on the distal side of said aperture, and urged toward said aperture, withdrawing the end of said catheter through said aperture and deploying an additional length of said wire in an elongated configuration to be exposed on the proximal side of said aperture, whereupon said continued deployment, said wire is permitted to assume a preprogrammed configuration, including an opposing occlusion-forming wire segment urged toward said aperture on the proximal side of the aperture, and disengaging the wire from the means for holding said wire.

12. A method as recited in claim 11, wherein said defect is a atrial septal defect.

13. A method as recited in claim 11, wherein said defect is a ventricular septal defect.

14. A method as recited in claim 11, wherein said defect is a patent ductus arteriosus.

* * * * *

US005108420C1

(12) EX PARTE REEXAMINATION CERTIFICATE (5118th)
United States Patent
Marks

(10) Number: US 5,108,420 C1
(45) Certificate Issued: Jun. 7, 2005

(54) APERTURE OCCLUSION DEVICE

(75) Inventor: Lloyd A. Marks, 301 Roanoke Rd., Westfield, NJ (US) 07090

(73) Assignee: Lloyd A. Marks, Westfield, NJ (US)

Reexamination Request:
No. 90/006,043, Jun. 25, 2001

Reexamination Certificate for:
Patent No.: 5,108,420
Issued: Apr. 28, 1992
Appl. No.: 07/649,593
Filed: Feb. 1, 1991

(51) Int. Cl.$^7$ ............................................. A61B 17/00
(52) U.S. Cl. ....................... 606/213; 606/151; 606/157; 606/78
(58) Field of Search ........................................ 606/213

(56) References Cited

U.S. PATENT DOCUMENTS

| | | | |
|---|---|---|---|
| 3,620,212 A | | 11/1971 | Fannon ........................ 128/130 |
| 4,503,569 A | * | 3/1985 | Dotter |
| 4,649,922 A | * | 3/1987 | Wiktor |
| 4,665,906 A | | 5/1987 | Jervis ............................ 606/78 |
| 4,776,337 A | * | 10/1988 | Palmaz |
| 4,832,055 A | | 5/1989 | Palestrant .................... 128/899 |
| 4,836,204 A | | 6/1989 | Landymore et al. ......... 128/334 |
| 4,917,089 A | | 4/1990 | Sideras ........................ 606/215 |
| 4,994,069 A | | 2/1991 | Ritchart ....................... 606/191 |
| 5,192,301 A | | 3/1993 | Kamiya et al. |

FOREIGN PATENT DOCUMENTS

| | | |
|---|---|---|
| AU | 79531 | 3/1975 |
| DE | 233 303 | 2/1986 |

OTHER PUBLICATIONS

"Transcatheter Closure of Atrial Septal Defects," Lock et al., Circulation, vol. 79, No. 5, May 1989.
Letter from Defendant AGA's Attorney dated Oct. 14, 2004 (3–pages).
Letter from Defendant AGA's attorney (2–pages).
"Secundum Atrial Septal Defect," T. King et al., JAMA, vol. 235, No. 23, pp. 2506–2509, Jun. 1976.
"Double–Umbrella Closure of Atrial Defects", Rome et al., Circulation, vol. 82, No. 3, Sep. 1990.
"Transvenous Atrial Septal Defect Occlusion . . . ", Sideris et al., Circulation, vol. 81, No. 1, Jan. 1990.
"Transvenous Atrial Septal Defect Occlusion . . . ", Sideris et al., Am. J. Cardiol., vol. 66, Dec. 1990.
"Transcatheter Therapy for Congenital Heart Disease", Hellenbrand, Cardiology Clinics, vol. 6, No. 3, Aug. 1988.
"Nonoperative Closure of Left–to–Right Shunts", Mills et al., J. Thoratic & Cardiovascular Surgery, vol. 72, No. 3, Sep. 1976.
"Nonoperative Closure of Atrial Septal Defects", King et al., Surgery, vol. 75, No. 3, Mar. 1974.
"Secundum Arial Septal Defect", King et al., JAMA, vol. 235, No. 23, Jun. 1976.
"Transcatheter Treatment of Congenital Heart Disease", Rashkind, Circulation, vol. 67, No. 4, Apr. 1983.
"Transcatheter Closure of Ventricular Septal Defects", Lock et al., Circulation, vol. 78, No. 2, Aug. 1988.
"Interventional Cardiac Catheterization in Congenital Heart Disease", Rashkind, Int'l J. Cardiol., 1985.
"Transcatheter Closure of Patent Ductus Arteriosus", Latson et al., Nebraska Med. J., Feb. 1987.

(Continued)

*Primary Examiner*—Michael N. Thaler

(57) ABSTRACT

A device consisting of a wire for occluding an aperture within a body surface, such as atrial and ventricular septal defects (and the method of using such a device). The wire comprises two configurations, an elongated configuration for passage into said body through a catheter and through the aperture, and a preprogrammed configuration including occlusion-forming wire segments, one on each side of said aperture. The wire also includes means (preferably a temperature-induced shape change) for changing the wire from the elongated configuration to the preprogrammed configuration in the body.

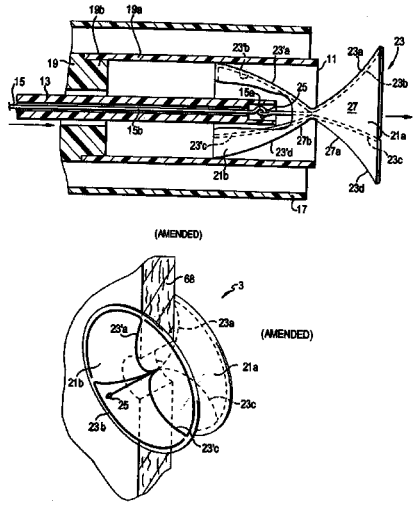

OTHER PUBLICATIONS

"Transcatheter Closure of PDA in Piglets", Lock et al., American J. Cardiol., vol. 55, Mar. 1985.
"Transcatheter Umbrella Closure of Congenital Heart Disease", Lock et al., Circulation, vol. 75, No. 3, Mar. 1987.
"Development of a New Transvenous PDA Occlusion Technique Using a Shape Memory Polymer", Echigo et al, ASAIO Transactions 1990.
"Development of Device Made of Shape Memory Polymer . . . ", Echigo et. al, Proceedings of Japan Society for Artificial Organs, Aug. 1989.
"Transcatheter Closure of Atrial Septal Defects", Babic et al., The Lancet, Sep. 1990.
"A New Device for Transcatheter Closure of the PDA", Magal et al., Invest. Radiol., 1989.
Defendant's Motion for Summary Judgment Under Rule 56.
Defendant's Memorandum in Support of Its Motion for Summary Judgment Under Rule 56.
Memorandum in Reply to Plaintiffs' Opposition.
Defendant's Renewed Motion for Summary Judgment Under Rule 56.
Defendant's Memorandum in Support of Its Renewed Motion.
Defendant's Reply to Plaintiff's Opposition to Defendant's Motion for Summary Judgment Under Rule 56.

* cited by examiner

US 5,108,420 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, line 55 to column 4, line 8:

Aperture occlusion device 27 is composed of two biocompatible membranes 21a and 21b, each comprised of a thin polyurethane membrane film, for example. Preprogrammed shape memory retentive, wire ribs 23 [and 23'] are secured (and may be threaded, sewn or sandwiched) to each biocompatible membrane 21a and 21b. Eye 25, attached to wire ribs 23 [and 23'], extends from the center of aperture occlusion device 27 and engages knuckle 15a of release wire 15. One half of aperture occlusion device 27b is seen in the folded state; upon release from deployment catheter 19 and contact with body temperature, the membrane expands between the ribs, as shown by device half 27a with associated ribs 23. In FIG. 1, four wire ribs, 23a–d and 23'a–d, on each half of device 27, unfold, i.e. are converted from their elongated configuration to a second preprogrammed configuration, such as by a thermally stimulated shape change to a preprogrammed configuration, which urges the wire ribs outwardly, to expand and release. For this purpose, ribs 23a–d and 23'a–d are composed of a thermally responsive shape, shape memory retentive material, such as nitinol.

Column 5, lines 7–11:

FIG. 4 is a cross-section through plane 4—4 of FIG. 3. As depicted therein, membrane [21a] *21b* is secured to rib [23a] *23'c* by glue 23e. Stitches, staples or the like may also be used to affix membrane [21a] *21b* to rib [23a] *23'c*. Other configurations of ribs 23a, b, c may also be used.

THE DRAWING FIGURES HAVE BEEN CHANGED AS FOLLOWS:

Amend the showing of FIG. 1 to illustrate the wire rib 23b, 23'b and the wire rib 23c, 23'c in dashed lines as continuous wires extending from one end of the device 27 to the other.

Amend the showing of FIG. 1 to illustrate the four wire ribs generally with reference numeral 23 and a lead arrow as shown.

Amend the showing of FIG. 2 to change reference numeral "23b" to reference numeral —23a— and to change reference numeral "23a" to reference numeral —23c—.

Amend the showing of FIG. 4 to change reference numeral "21a" to reference numeral —21b— and to change reference numeral "23" to reference numeral —23'c—.

Amend the showing of FIG. 5 to illustrate the wire rib 23a, 23'a and the wire rib 23b, 23'b as continuous wires extending from one side of the aperture 68 to the other.

AS A RESULT OF REEXAMINATION, IT HAS BEED DETERMINED THAT:

The patentability of claims 1–14 is confirmed.

New claims 15–67 are added and determined to be patentable.

1. A device adapted to occlude an aperture within a body surface, and adapted to be passed into said body, through a catheter and through said aperture, said device comprising a wire having two configurations, an elongated configuration for passage through said catheter and through said aperture, and a preprogrammed configuration which includes occlusion-forming wire segments one on each side of said aperture urged toward one another and means for causing said wire to change from said elongated configuration to said preprogrammed configuration inside said body, said means being a temperature responsive material of construction of said wire, by which said wire is activated at body temperature, to assume said preprogrammed configuration.

*15. A device according to claim 1, including a plurality of said wires and a plurality of occlusion-forming wire segments on each side of said aperture.*

*16. A device according to claim 15, wherein said wires consist of nitinol.*

*17. A device according to claim 16, including a membrane attached to the wire segments on each side of said aperture.*

*18. A device according to claim 15 wherein said wire segments have a helical form.*

*19. A device according to claim 1, including a plurality of occlusion-forming wire segments on each side of said aperture.*

*20. A device according to claim 19, including a membrane attached to the wire segments on each side of said aperture.*

*21. A device according to claim 20, wherein said membrane and said wire segments form a domed member on each side of said aperture in the preprogrammed configuration.*

*22. A device according to claim 21, wherein said domed member is outwardly convex.*

*23. A device according to claim 21, wherein said domed member is substantially in the shape of an elliptical half rotated through 360° about one end of its long axis.*

*24. A device according to claim 21, wherein said domed member has a curved surface substantially in the shape of an arc rotated through 360° about one of its ends such that said one end defines the center of the curved surface and the other end defines the circumference of the curved surface.*

*25. A device according to claim 20, wherein said wire segments consist of nitinol.*

*26. A device according to claim 20, wherein said wire segments have a helical form.*

*27. A device according to claim 1, including a membrane attached to the wire segments on each side of said aperture.*

28. A device according to claim 27, wherein said membrane and said wire segments form a domed member on each side of said aperture.

29. A device according to claim 28, wherein said domed member is outwardly convex.

30. A device according to claim 28, wherein said domed member is substantially in the shape of an elliptical half rotated through 360° about one end of its long axis.

31. A device according to claim 28, wherein said domed member has a curved surface substantially in the shape of an arc rotated through 360° about one of its ends such that said one end defines the center of the curved surface and the other end defines the circumference of the curved surface.

32. A device according to claim 27, wherein said wire segments consist of nitinol.

33. A device according to claim 1 wherein said wire segments have a helical form.

34. A device according to claim 9, wherein said means comprises said wire being composed of a shape memory retentive material.

35. A device according to claim 34, wherein said shape memory retentive material is one of spring steel or nitinol.

36. A device according to claim 34, wherein said shape memory retentive material is a thermally responsive shape memory material.

37. A device adapted to occlude an aperture within a body surface and adapted to be passed into said body through a catheter and through said aperture, said device comprising a wire having two configurations, an elongated configuration for passage through said catheter and through said aperture to be occluded, and a preprogrammed configuration which includes opposing occlusion-forming wire segments adapted to be deployed one on each side of said aperture to be occluded and urged toward one another and means for causing said wire to change from said elongated configuration to said preprogrammed configuration when the wire segments are deployed inside said body, said means being a temperature responsive material of construction of said wire by which said wire is activated at body temperature to assume said preprogrammed configuration in which each occlusion-forming wire segment is adapted to press toward the opposing occlusion-forming wire segment.

38. A device according to claim 37 wherein at least one wire segment is configured in the preprogrammed configuration to form a circular periphery with a center, said at least one wire segment extending from the center to the periphery.

39. A device according to claim 38 wherein said wire segments are configured in the preprogrammed configuration to form a circular periphery with a center, said wire segments extending from the center to the periphery.

40. A device according to claim 37 wherein said wire segments extend generally radially from a center of the device and form a circular periphery of the device in the preprogrammed configuration.

41. A device according to claim 40 wherein said wire segments extend along a radius from a center of the device and form a circular periphery of the device in the preprogrammed configuration.

42. A device according to claim 37 wherein said device has a circular periphery with a center, at least one wire segment extending from the center then curving and extending circumferentially to the periphery of the device in the preprogrammed configuration.

43. A device according to claim 42 wherein said device has a circular periphery with a center, said wire segments extending from the center then curving and extending circumferentially to the periphery of the device in the preprogrammed configuration.

44. A device according to claim 37 wherein each wire segment forms an outwardly convex generally dome-shaped member in the preprogrammed configuration.

45. A device according to claim 44 wherein said dome-shaped member includes a membrane supported by said wire segments.

46. A device according to claim 37 wherein said occlusion-forming wire segments comprise helical coils urged toward one another.

47. A device adapted to occlude an aperture within a body surface and adapted to be passed into said body through a catheter and through said aperture to be occluded, said device comprising a wire having two configurations, an elongated configuration for passage through said catheter and through said aperture to be occluded, and a preprogrammed configuration which includes occlusion-forming wire segments adapted to be deployed one on each side of said aperture, and means for causing said wire to change from said elongated configuration to said preprogrammed configuration when the wire segments are deployed inside said body, wherein said occlusion forming wire segments each comprise helical coils urged toward one another, and wherein said wire segments in the preprogrammed configuration are configured to form a device having a circular periphery with a center, said wire segments extending from the center to the periphery of said device.

48. A device according to claim 47 wherein each wire segment forms an outwardly convex generally dome-shaped member in the preprogrammed configuration.

49. A device according to claim 47 wherein the wire segments of the helical coils spiral inwardly from the periphery to the center of said device in the preprogrammed configuration.

50. A device according to claim 47 wherein said wire segments form an outermost periphery of the circular device, the wire segments of the outermost periphery of the circular device configured to engage and press against the body surface surrounding the aperture in the preprogrammed configuration.

51. A device adapted to occlude an opening within a body surface and adapted to be passed into said body, through a catheter and into said opening to be occluded, said device comprising a wire having two configurations, an elongated configuration for passage through said catheter and into said aperture to be occluded, and a preprogrammed configuration which includes occlusion-forming wire segments adapted to be deployed one on each side of said aperture, and means for causing said wire to change from said elongated configuration to said preprogrammed configuration when the wire segments are deployed inside said body, wherein said occlusion-forming wire segments comprise helical coils urged toward one another, and wherein said wire segments are configured to form an outer circular periphery that extends beyond the boundary of the opening, said device also including a relatively narrow waist adapted to be disposed in the opening and at least some of said wire segments extending from the relatively narrow waist to the outer circular periphery of said device in the preprogrammed configuration.

52. A device adapted to occlude an aperture within a body and adapted to be passed into said body through a catheter and into said aperture, said device comprising a wire having two configurations, an elongated configuration in which the wire is adapted to pass through said catheter and into said aperture to be occluded, and a preprogrammed configuration in which opposing occlusion-forming wire segments of said wire are adapted to be deployed one on each side of said aperture, said wire segments being urged toward one another when the wire is in said preprogrammed configuration, and means for causing said wire to change from said elongated configuration to said preprogrammed configuration when the wire is deployed inside said body, said means comprising a wire constructed of a temperature responsive material responsive at body temperature to assume said preprogrammed configuration.

53. The device of claim 52 further comprising a membrane attached to the wire segments that extends radially beyond and occludes the aperture.

54. The device of claim 53 further comprising stitches that attach the membrane to the wire segments.

55. The device of claim 53 wherein the wire segments and membrane form an outwardly convex generally dome-shaped member in the preprogrammed configuration on each side of the aperture.

56. A device adapted to occlude an aperture within a body and adapted to be passed into said body through a catheter and into said aperture, said device comprising a wire having two configurations, an elongated configuration in which the wire is adapted to pass through said catheter and into said aperture to be occluded, and a preprogrammed configuration in which opposing occlusion-forming wire segments of said wire are adapted to be deployed one on each side of said aperture, said wire segments being urged toward one another when the wire is in said preprogrammed configuration, said wire being composed of a temperature responsive material which changes from said elongated configuration to said preprogrammed configuration at body temperature.

57. The device of claim 56 further comprising a membrane attached to the wire segments that extends radially beyond and occludes the aperture.

58. The device of claim 57 further comprising stitches that attach the membrane to the wire segments.

59. The device of claim 57 wherein the wire segments and membrane form an outwardly convex generally dome-shaped member in the preprogrammed configuration on each side of the aperture.

60. A device adapted to occlude an aperture within a body and adapted to be passed into said body through a catheter and into said aperture, said device comprising a wire and a membrane supported by said wire, said wire having two configurations, an elongated configuration in which the wire and membrane are adapted to pass through said catheter and into said aperture to be occluded, and a preprogrammed configuration in which the membrane and opposing occlusion-forming wire segments are adapted to be deployed to occlude said aperture with one wire segment on each side of said aperture, said wire segments being urged toward one another when the wire is in said preprogrammed configuration, and means for causing said wire to change from said elongated configuration to said preprogrammed configuration when the wire is deployed inside said body, said means comprising a wire constructed of a temperature responsive material responsive at body temperature to assume said preprogrammed configuration.

61. The device of claim 60 further comprising stitching that secures the membrane to the wire.

62. The device of claim 60 further comprising a plurality of wires wherein said membrane is secured to more than one wire.

63. A collapsible medical device, comprising a plurality of metal wires and a membrane attached to the wires, said device forming an occlusive member adapted to occlude an opening in a body surface having a first side and a second side, said wires having an expanded preprogrammed configuration shape adapted to be disposed on each of the first and second sides of the opening such that the membrane and the wires are urged toward one another and cooperate to occlude the opening, said device being deformable to an elongated configuration with a lesser cross-sectional dimension for delivery through a channel in a patient's body, and means for causing said wires to change from said elongated configuration to said preprogrammed configuration when the wire is deployed inside said body, said means comprising a wire constructed of a temperature responsive material responsive at body temperature to assume said preprogrammed configuration after delivery to the opening in the body surface.

64. The collapsible medical device of claim 63 wherein the membrane extends radially beyond and occludes the opening.

65. The collapsible medical device of claim 63 further comprising stitches that attach the membrane to the wires.

66. The collapsible medical device of claim 63 wherein the wire and membrane on each of the first and second sides form an outwardly convex generally dome-shaped member in the preprogrammed configuration.

67. The collapsible medical device of claim 63 wherein the wire includes a wire segment adapted to be deployed on the first side of the opening and another wire segment adapted to be deployed on the second side of the opening, said wire segments opposing one another and being adapted to press toward one another to thereby occlude the opening.

* * * * *